US012637681B2

(12) United States Patent
Deng et al.

(10) Patent No.: US 12,637,681 B2
(45) Date of Patent: May 26, 2026

(54) BACTERICIDAL PHAGE VECTORS

(71) Applicant: Helmholtz Zentrum München Deutsches Forschungszentrum für Gesundheit und Umwelt (GmbH), Neuherberg (DE)

(72) Inventors: Li Deng, Mondsee (AT); Haiying Huang, Neufahrn bei Freising (DE); Jinling Xue, Munich (DE)

(73) Assignee: Helmholtz Zentrum München Deutsches Forschungszentrum für Gesundheit und Umwelt (GmbH), Neuherberg (DE)

( * ) Notice: Subject to any disclaimer, the term of this patent is extended or adjusted under 35 U.S.C. 154(b) by 1051 days.

(21) Appl. No.: 17/641,880

(22) PCT Filed: Sep. 10, 2020

(86) PCT No.: PCT/EP2020/075289
§ 371 (c)(1),
(2) Date: Mar. 10, 2022

(87) PCT Pub. No.: WO2021/048257
PCT Pub. Date: Mar. 18, 2021

(65) Prior Publication Data
US 2022/0333120 A1      Oct. 20, 2022

(30) Foreign Application Priority Data

Sep. 11, 2019    (LU) ....................................... 101383

(51) Int. Cl.
*C12N 15/64* (2006.01)
*C12N 15/74* (2006.01)

(52) U.S. Cl.
CPC ............. *C12N 15/64* (2013.01); *C12N 15/74* (2013.01); *C12N 2795/00021* (2013.01); *C12N 2795/00041* (2013.01); *C12N 2795/00051* (2013.01)

(58) Field of Classification Search
None
See application file for complete search history.

(56) References Cited

FOREIGN PATENT DOCUMENTS

| | | | | | |
|---|---|---|---|---|---|
| EP | 2292245 A1 | * | 3/2011 | .............. | C12N 7/00 |
| JP | 6416803 B2 | | 10/2018 | | |
| WO | WO 2007/130655 A2 | | 11/2007 | | |
| WO | WO 2013/068743 A1 | | 5/2013 | | |
| WO | WO 2019/140534 A1 | | 7/2019 | | |
| WO | WO 2021/048257 A1 | | 3/2021 | | |

OTHER PUBLICATIONS

Lu et al. (Proceedings of the National Academy of Sciences 106.12 (2009): 4629-4634. (Year: 2009).*
Oechslin et al. (The Journal of infectious diseases 215.5 (2017): 703-712. (Year: 2017).*
Kusradze et al. (Frontiers in microbiology 7 (2016): 1590. (Year: 2016).*
Džunková et al. (Nature Microbiology 4.12 (Published online: Aug. 5, 2019): 2192-2203. (Year: 2019).*
Yang et al. (MSystems 4.2 (Published: Apr. 16, 2019): 10-1128. (Year: 2019).*
Schwarzl et al. (Journal of Molecular Biology 427.21 (2015): 3368-3374. (Year: 2015).*
Hyman et al. (Pharmaceuticals 12.1 (Published: Mar. 11, 2019): 35 (Year: 2019).*
International Search Report and Written Opinion for Application No. PCT/EP2020/075289, mailed Dec. 22, 2020.
International Preliminary Report on Patentability for Application No. PCT/EP2020/075289, mailed Mar. 24, 2022.
Bhattarai et al., Engineered phage-based therapeutic materials inhibit *Chlamydia trachomatis* intracellular infection. Biomaterials. Jul. 2012;33(20):5166-74. doi: 10.1016/j.biomaterials.2012.03.054. Epub Apr. 9, 2012.
Deng et al., Contrasting life strategies of viruses that infect photo- and heterotrophic bacteria, as revealed by viral tagging. mBio. Oct. 30, 2012;3(6):e00373-12. doi: 10.1128/mBio.00373-12.
Džunková et al., Defining the human gut host-phage network through single-cell viral tagging. Nat Microbiol. Dec. 2019;4(12):2192-2203. doi: 10.1038/s41564-019-0526-2. Epub Aug. 5, 2019.
Lu et al., Engineered bacteriophage targeting gene networks as adjuvants for antibiotic therapy. Proc Natl Acad Sci U S A. Mar. 24, 2009;106(12):4629-34. doi: 10.1073/pnas.0800442106. Epub Mar. 2, 2009.
Oechslin et al., Synergistic Interaction Between Phage Therapy and Antibiotics Clears *Pseudomonas aeruginosa* Infection in Endocarditis and Reduces Virulence. J Infect Dis. Mar. 1, 2017;215(5):703-712. doi: 10.1093/infdis/jiw632.
Abedon et al., Phage treatment of human infections. Bacteriophage. Mar. 2011;1(2):66-85. doi: 10.4161/bact.1.2.15845.
Milanesi et al., Transcriptions of the Bacteriophage T4 Template in Vitro: Separation of "Delayed Early" from "Immediate Early" Transcription. Proc Natl Acad Sci U S A. May 1970;66(1):181-8. doi: 10.1073/pnas.66.1.181.
Pero et al., Restriction Cleavage Map of SP01 DNA: General Location of Early, Middle, and Late Genes. J Virol. Jul. 1979;31(1):156-71. doi: 10.1128/JVI.31.1.156-171.1979.
Uchiyama et al., Characterization of *Helicobacter pylori* bacteriophage KHP30. Appl Environ Microbiol. May 2013;79(10):3176-84. doi: 10.1128/AEM.03530-12. Epub Mar. 8, 2013.

* cited by examiner

*Primary Examiner* — Maria G Leavitt
*Assistant Examiner* — Brendan Thomas Tinsley
(74) *Attorney, Agent, or Firm* — Wolf, Greenfield & Sacks, P.C.

(57)      ABSTRACT

The present invention relates to a method for preparing a bactericidal phage vector, (pharmaceutical) compositions comprising such phage vectors, also for use in treating diseases, particularly those caused by (antimicrobial resistance) bacterial cells.

10 Claims, 2 Drawing Sheets

BACTERICIDAL PHAGE VECTORS

RELATED APPLICATIONS

Figure 1:
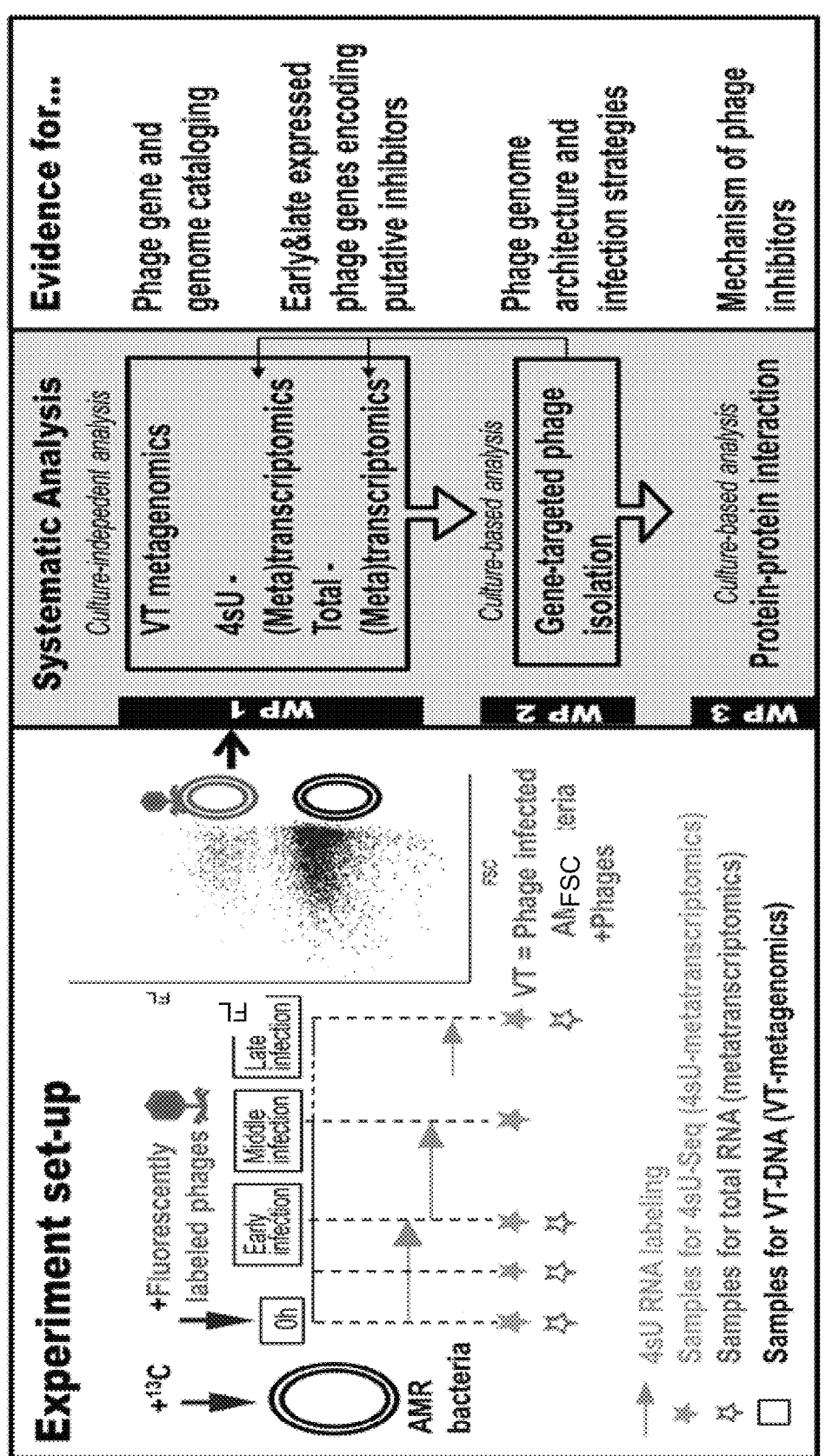

This application is a national stage filing under 35 U.S.C. § 371 of international application number PCT/EP2020/075289, filed Sep. 10, 2020, which claims priority to Luxembourg application number LU 101383, filed Sep. 11, 2019, the content of which is herein incorporated by reference in its entirety.

The present invention relates to a method for preparing a bactericidal phage vector, (pharmaceutical) compositions comprising such phage vectors, also for use in treating diseases, particularly those caused by (antimicrobial resistance) bacterial cells.

Antimicrobial resistance (AMR) is a major threat to global health and global economies. Worldwide, Infections by multidrug-resistant bacteria are estimated to kill more than 700,000 people, including 25,000 cases in Europe and 23,000 cases in the US every year (Laximinarayan et al., The Lancet Infect Diseases (2013), 13: 1057-1098). Antimicrobial resistance also places a tremendous burden on healthcare systems and society, with an annual cost due to healthcare expenditures and productivity losses estimated by the European Commission at approximately €1.5 billion in the EU.

To tackle this challenge, bacteriophages, viruses that infect bacteria, can be employed to fight AMR as a complement to antibiotic therapy (Salmond et al., Nat Rev Micro (2015), 13: 777-786). Studies revealed that phages are the most abundant biological entities on Earth, with $\sim 10^{31}$ phages in total and $10^{23}$ phage infections per second. Phages are highly specific in their choice of bacterial hosts, mediated by specific receptor proteins, thus will cause no collateral damage to the microbial companions that form our microbiome, which is increasingly appreciated as essential to our health (Shreiner et al., Curr Op Gastroenterol (2015), 31: 69-75). After over a billion years of co-evolutionary struggle with their bacterial hosts, phages have evolved highly diverse proteins that inhibit or 'hijack' bacterial metabolic processes to their own benefit. Coupling the bactericidal effects to host-recognition machineries, promising progress has been made in treating AMR bacteria using: i) lytic phages which can directly lyse hosts or a cocktail of different lytic phages to overcome bacterial resistance, such as a cocktail of phages used to treat *Pseudomonas aeruginosa* ear infections and a European phase I/II clinical trial investigating phages for the treatment of burn wounds infected with *Escherichia coli* and *P. aeruginosa* (Oechslin et al., J Infect Dis (2017), 215: 703-712) ii) phage-encoded bactericidal peptides or enzymes, such as endolysins, which are peptidoglycan hydrolases involved in cell lysis during phage replication (preclinical trials and phase I, II clinical trials are underway on *Staphylococcus aureus*) (Roach et al., Bacteriophage (2014), 509: S9).

Most of such phage therapy progress so far, however, has been derived from a still very limited number of phage isolates, which slows down development of new phage therapies as valid therapeutics. Among the $10^{31}$ phages on earth, only approx. 2000 specimen are isolated and sequenced (NCBI). Insight is still limited to those phages that could be cultured.

Identification of bacteriophage hosts is essential for understanding patterns of bacterial mortality and horizontal gene transfer (HGT). Knowledge of host-phage networks beyond the limitation of culture-based methods is important for assessing target-specificity of e.g. bioengineered phages used in the treatment of infections caused by antibiotic resistant bacteria or for the remediation of microbiome dysbioses5.

These and further disadvantages need to overcome. The present invention therefore addresses these needs and technical objectives and provides a solution as described herein and as defined in the claims.

The present invention relates to a method for preparing a bactericidal phage vector, comprising the following steps:

(1) Labelling phages, (2) Contacting the labelled phages of (1) with bacterial cells for which a bactericidal effect of said bactericidal phage vector is desired under conditions which allow infection of said bacterial cells with said labelled phages, (3) Identifying and separating bacterial cells being infected with labelled phages, (4) Metagenomic sequencing of phages in infected bacterial cells of (3), including bioinformatics analysis to map the genetic relatedness of phages of (3) according to nucleic acid and/or amino acid sequence similarity or identity levels, and allocate phages of (3) into different genetic clusters, (5) 4-sU- and total metatranscriptomic sequencing of RNA of early, middle and late expressed phage genes in said infected bacterial cells, map RNA reads to the sequences of (4), (6) Selecting two or more suitable marker genes, wherein the suitable marker genes are ORFs (a) showing >about 95% (or 96, 97, 98, or 99%) ANI (average nucleotide identity) or AAI (average amino acid identity) (preferably ANI) within one cluster of (4), and/or (preferably "and")<about 75% (or 70, 65, or 60%) ANI or AAI (average amino acid identity) (preferably ANI) compared to one or more other clusters of (4); and/or (b) exhibiting at least about 2-fold (or 2.5-fold, or 3-fold, or 3.5-fold, or 4-fold) expression in early and late infection compared to the average expression level of all RNAs of (5), optionally (in one embodiment of the present invention, preferably or mandatorily) followed by further bioinformatic analysis for potential further functions of the marker gene, (7) Targeted phage isolation based on said one or more selected marker genes of (6), (8) Identification of candidate genes for bactericidal effect on the infected host cell, and (9) Preparing a phage vector comprising one or more candidate genes of (8).

As used herein, the term "phage vector" comprises particularly complete phages or parts or fragments thereof, or nucleic acid vectors (e.g., DNA or RNA nucleic acid molecules, single- or double stranded, linear or circular, natural or synthetic) including plasmids, cosmids, shuttle vectors, and the like.

Labeling of phages as defined in step (1) of the method of the present invention may be performed by any method known in the art suitable to label—and thereafter—detect phages—Examples of such labeling methods may comprise fluorescent labelling, antibody labelling and radioactive labelling (see, e.g., Džunková et al., Nature Microbiol (2019), DOI: 10.1038//s41564-019-0526-2). Labeling of phages as defined in step (1) may include labeling the phages with a detectable label.

Potential sources of phages to be labeled according to step (1) of the method of the present invention may comprise inter alia natural environments, clinical samples, wastewater treatment plants, or hospital waste resources.

Contacting the labelled phages in step (1) of the method of the present invention with bacterial cells for which a bactericidal effect of said bactericidal phage vector is desired can be carried out by any suitable method known in the art and as also described and exemplified herein. Generally, in accordance with the present invention, this contacting step is carried out under conditions which allow infection of said bacterial cells with said labelled phages. As is readily clear for the skilled person, such conditions individually depend on the nature of bacteria for which a bactericidal effect of said bactericidal phage vector is desired. Means and methods for phage cultivation and/or infection are, e.g. described in Džunková et al., Nature Microbiol (2019), DOI: 10.1038//s41564-019-0526-2, Deng et al., Nature (2014), 513, 242-245 Deng et al. (2012), mBio 3, e00373-12. doi:10.1128/mBio.00373-12.

Identification and separation of bacterial cells being infected with labelled phages as defined in step (3) of the method described and provided in context with the present invention may comprise any suitable method for cell identification and separation known in the art, e.g., FACS (fluorescence-activated cell sorting), more particularly single-cell FACS. Such method may be particularly suitable to be employed in accordance of the present invention the host bacteria cell tagged with a labeled phage exhibits higher fluorescence from the labeled phages and can thus be separated from non-tagged bacteria cells as well as from free phages. For example, in accordance with the present invention, each fluorescence-activated event may be sorted into (i) a single well of a multi (e.g., 96- or 384)-well-plate, thus each well contains one bacteria and the infecting phage(s); or (ii) a collective container for multiple infected bacteria and phages. Identification and separation of bacterial cells being infected with labelled phages as defined in step (3) of the method described and provided in context with the present invention may comprise identifying and separating the bacterial cells based on detection of the detectable label.

The identification of the marker genes as defined in step (6) of the method of the present invention requires information on the genome of the phages that infect the bacterial cells in step (3) as well as information on the transcribed RNA in the bacterial cells.

First, we will explain how the information on the genome of the phages is acquired. This can be achieved by using metagenomic sequencing, such as metagenomics sequencing as defined in step (4) of the method of the present invention. Metagenomics methods may use genomic DNA from many different organisms, usually within a microbiome. Metagenomics can be seen as another useful bioinformatic tool to access the genetic information from entire community of organisms. It is also a powerful tool for generating novel findings about microbial functions. Using metagenomics, functional gene composition of microbial communities can be accessed. Thomas et al.'s "Metagenomics—A guide from sampling to data analysis" gives us a flow diagram of a typical metagenome project, containing the following steps: experimental design, sampling, sample fractionation, DNA extraction, DNA sequencing, assembly, binning, annotation, statistical analysis, data storage, metadata and data sharing (Thomas, T.; Gilbert, J.; Meyer, F. (2012). "Metagenomics—A guide from sampling to data analysis". Microbial Informatics and Experimentation 2 (1): 3. doi:10.1186/2042-5783-2-3).

Metagenomics is useful in studying DNA of uncultured organisms. A metagenome may be the entire genetic information of a group of organisms. Metagenomics can be done on samples collected from soil, sea water, sea bed, air, animal waste, etc. The metagenomic processing pipeline may involve sample collection; DNA read sequencing, sequence comparison to the reference genome, comparison file and interactive analysis and visualization. Sequence comparison is done using BLAST, Megablast, BLAT and SSAHA. Identification of species by DNA can be done by using BLAST. Then analysis based on NCBI taxonomy may be done. Megan metagenome analyzer is the functional analysis using the SEED classification. IMG/M and MG-RAST are different metagenomic analysis tools. Metagenomics may involve binning. Binning is process in which DNA sequences are sorted into groups that might represent an individual genome or genomes from closely related organisms. Binning can be composition based or similarity based.

The metagenomic sequencing as defined in step (4) of the method of the present invention can be done by any suitable method known in the art and as also described and exemplified herein. For example, generally, either viral tagging (VT) or purified viral samples may be subject to conditions to degrade free bacterial nucleotides in the viral filtrate (e.g., using DNAse or other nucleases). Afterwards, viral nucleotides (e.g., viral DNA or RNA) may be extracted by methods known in the art, followed by virion lysis. The DNA may then be purified and sequenced, e.g., with next gen sequencing methods known in the art. For bioinformatic analysis to map the genetic relatedness of phages according to nucleic acid and/or amino acid sequence similarity or identity (e.g., average nucleotide/amino acid identity (ANI/AAI) metrics (see, e.g., Konstantinidis et al., PNAS (2005), 102: 2567-2572), or Deng et al., Nature (2014), 513: 242-245), and other machine-learning methods), for example, contigs may be assembled from post-QC reads as known in the art and suitable contigs be selected, followed by ORF (open reading frame) assignment using ORF prediction systems known in the art. ORFs may then be clustered as known in the art and also exemplified herein (e.g., using CD-HIT by Weizhong; http://weizhongli-lab.org/cd-hit/ or http://bioinformatics.org/cd-hit/) and a suitable cut-off be defined (e.g., particularly for using CD-HIT for clustering, a cut-off of about 75% identity). Thus, step (4) of the method of the present invention can be seen as providing the information necessary for selection of the two or more marker genes as defined in step (6)(a) of the method of the present invention.

To select the two or more marker genes as defined in step (6) of the method of the present invention, more time-resolved transcriptomic sequence information is necessary. This involves the sequencing of the 4-sU- and total metatranscriptomic sequencing of RNA of early, middle and late expressed phage genes. This is done in step (5) of the method of the present invention and can be seen as time-resolved sequencing of total RNA. Combining 4-sU- and total metatranscriptomic sequencing of RNA allows for a time-resolved metatranscriptomic analysis of gene expression patterns at certain points of time, such as early, middle and late phase of phage infection.

In the 4-sU-metratranscriptomic sequencing approach, cell culture samples may be cultured with tagged nucleotides which allow for selective purification of newly synthesized RNA molecules. This approach may include pulse labeling with 4-thiouridine (4-sU), a uracil analogue that is incorporated in newly synthesized RNA molecules. In this type of experiment, a person skilled in the art would supplement cells with 4-sU at the time of the experiment or shortly beforehand, e.g. at the beginning of early, middle or late phase of infection. When the experimental treatment presumably affects RNA expression, newly synthesized RNA would be labeled with 4-sU. This newly synthesized RNA is labeled with a reactive thiol group, making it possible to link useful molecules to the RNA. Biotin is a popular molecule for use in this type of assay. Incubation of biotinylated RNA with beads containing streptavidin allows for the selective purification of newly synthesized RNA. From here, newly synthesized and total RNA are sequenced separately and compared for differences.

4-sU- and total metatranscriptomic sequencing of RNA of early, middle and late expressed phage genes (for general clustering of early-middle-late viral genes see, e.g., Pero et al., J Virol (1979), 31: 156-171) in said infected bacterial cells as defined in step (5) of the method of the present invention, followed by mapping RNA reads to the sequences of (4), can be performed by any suitable method known in the art and as also described and exemplified herein. For example, in accordance with the present invention, metabolic labeling of newly transcribed RNA with 4sU can be done as described in Rädle et al. (J Vis Exp (2013), 87: 50195; DOI: 10.3791/50195), or Davari (J Vis Exp (2018), 133: 56752, DOI: 10.3791/56752), or as exemplified in the examples. Mapping of RNA reads may be done, e.g., as described in Bonfert et al. (BMC Bioinformatics (2015), 16: 122) or as exemplified herein in the examples. Thus, step (5) of the method of the present invention can be seen as providing the information necessary for selection of the two or more marker genes as defined in step (6)(b) of the method of the present invention.

The selection of the marker genes as defined in step (6) of the method of the present invention can be seen as allowing isolating the phages from the "phage pool" of the phages present, e.g., in a sample that may be used in the method of the invention. The selection of the two or more marker genes is based on the following: first, two marker genes are selected, which are from the same cluster identified in step (4) and show a sequence similarity of >about 95% but do share less than about 75% sequence identity with genes from another cluster. Additionally or alternatively, the marker genes are expressed at least about 2-fold in early and late infection stages compared to the average expression level of all RNAs of step (5). This allows selecting marker genes that may originate from phages and not from the bacteria.

Selecting two or more suitable marker genes as defined in step (6) of the method of the present invention, wherein the suitable marker genes are ORFs (a) showing >about 95% (or 96, 97, 98, or 99%) ANI (average nucleotide identity) or AAI (average amino acid identity) (preferably ANI) within one cluster of (4), and/or (preferably "and")<about 75% (or 70, 65, or 60%) ANI or AAI (average amino acid identity) (preferably ANI) compared to one or more other clusters of step (4); and/or (preferably "and")

(b) exhibiting at least about 2-fold (or 2.5-fold, or 3-fold, or 3.5-fold, or 4-fold) expression in early and late infection stages compared to the average expression level of all RNAs of step (5), can be done by any suitable method known in the art. As regards step (6)(a), the sequence comparison can be done, e.g., as described herein (cf. also step (4) and the description for clustering (e.g., using CD-HIT)). Accordingly, in context with the present invention, a candidate marker gene may be considered a suitable marker gene if it is a (predicted) ORF which shows either at least or more than about 95% (or 96, 97, 98, or 99%) ANI (average nucleotide identity) or AAI (average amino acid identity) (preferably ANI) within one cluster as defined in step (4) of the method of the present invention, and/or maximum or less than about 75% (or 70, 65, or 60%) ANI or AAI (average amino acid identity) compared to one or more other clusters as defined in step (4) of the method of the present invention. In one embodiment of the present invention, a candidate marker gene is considered a suitable marker gene if it is a (predicted) ORF which shows more than about 95% ANI (average nucleotide identity) or AAI (average amino acid identity) (preferably ANI) within one cluster as defined in step (4) of the method of the present invention As regards step (6)(b) of the method of the present invention, the amount of transcribed RNA of the candidate marker gene is compared to the average level of all RNA as sequenced and mapped in step (5) of the method of the present invention. Such measurement of transcribed RNA amount can be performed by any suitable method known in the art, e.g., (q)RT-PCR or fluorometer (for 4sU). In accordance with the present invention, if the RNA amount of the candidate marker gene is at least about 2-fold (or 2.5-fold, or 3-fold, or 3.5-fold, or 4-fold) higher compared to the average amount of RNA sequenced and mapped in step (5), then such candidate marker gene can be considered as suitable marker gene.

The optional (in one embodiment of the present invention, mandatory) step of further bioinformatic analysis for potential further functions of the marker gene can also be done by any method known in the art which is suitable for assessing the function of a given gene. Such methods comprise comparing the sequence of a given gene with annotations of similar or identical genes of public databases as well as prediction systems or software (see, e.g., Hurwitz et al., PLoS One (2013), 8: e57355; Bolduc et al., Isme J (2016), 11: 7; or Elbehery et al., Frontiers in Microbiol (2018), 9: 1110/D01: 3389/fmicb.2018.01110).

Once the two or more suitable marker genes are identified in step (6) of the method of the present invention, the phages carrying those markers genes may be isolated in step (7) of the method of the present invention. The targeted phage isolation according to step (7) may be carried out by any method known in the art suitable to isolate phages based on selected gene or nucleic acid molecule sequences. As a general example in accordance with the present invention, single phage-bacteria pairs may be sorted onto solid bacterial lawns in multi-well plates and incubated under conditions allowing phage infection take place, agar from the infected area (plaque) may then be transferred to 2$^{nd}$ multi-well plates containing premixed (e.g., barcoded) primers for selected marker genes of step (6) of the method of the present invention, as well as PCR Master mix for PCR or qPCR. PCR products can be directly loaded in a gel and subject to sequencing (e.g., according to Sanger or other suitable sequencing methods known in the art), or pooled for next-generation sequencing. Samples from the positive wells may be subjected to further phage cultivation. As a more specific example in accordance with the present invention, such step (7) may be carried out as follows: (i) repeat step (1)-(3) of the present invention as described and defined herein, and sort each fluorescence-activated event (cell) into a single well of a multi (e.g., 96- or 384)-well-plate (Plate A) containing desired bacteria and growth medium, then subject to conditions which allow infection of said bacterial cells with said labelled phages. Aliquots from each well of Plate A may then be transferred into a new qPCR plate (Plate B) prefilled with primers of selected marker genes (selected in step (6) of the method of the present invention) for quantitative PCR. Phages in respective wells of Plate A corresponding to those in Plate B with positive yields may then be selected for further phage cultivation via liquid infection and clonal phages can be purified via classical double-layer agar plaque assay. Further suitable specific ways for targeted phage isolation are also exemplarily described herein in the examples.

After isolation of a relevant phage in step (7), the genes of genome of the isolated phage may be screened for genes showing a bactericidal effect. This may be gene for gene or by a more targeted approach based on a bioinformatic prediction of the function of each gene. The identification of candidate genes for bactericidal effect on the infected host cell as defined in step (8) of the method described and provided in context with the present invention can be carried out by any method known in the art suitable for identifying genes on their potential gene products' bactericidal properties and may vary depending on the desired effect as readily recognized by those of skill in the art. In accordance with the present invention, the general proceeding for this step (8) may preferably comprise gene-by-gene or protein-by-protein laboratory evaluation on bactericidal effect, and/or bioinformatic predictions based on annotations. For example in accordance with the present invention, such methods may comprise the following steps:

Highly expressed genes in early and late infection stages selected in (6) may be cloned into host bacteria using a single-copy, tight control expression shuttle vector. In particular, variable genes bioinformatically lacking functional assignment may be of interest. Since phages carrying such genes can be screened and isolated according to step (7) of the method of the present invention, clonal phages may be available for comparative proteomics analysis between phage-infected bacteria and phage-free bacteria, in order to further explore the molecular background of bactericidal effects of those enzymes/peptides. In this context, suitable molecular methods for protein-protein interaction analysis comprise, e.g. pull-down, yeast two-hybrid or bacteria two-hybrid interaction assays. Enzymes/peptides with extreme lethal activity which result in host cell death and/or no or substantially no gene expression can be achieved, may be subjected to further analysis, e.g., yeast expression system. Chemical methods, such as click chemistry, might also be employed if the resolution of the proteomics was not high enough.

Preparing a phage vector as defined in step (9) of the present invention may be done by any method suitable for preparing phages comprising defined genes of interest. For example, and in accordance with the present invention, a yeast-based phage synthetic platform, L-form based phage synthetic platform (cf., e.g., Kilcher et al., PNAS (2018), 115: 567-572) or cell-free synthetic platform (cf., e.g., Shin et al., ACS Synthetic Biol (2012), 1: 29-41/D01: 10.1021/sb2000165) may be employed. As used herein, in accordance with the present invention, when referring to "a" or "one" vector, this may also comprise multiple vectors or an array of vectors, where one or more genes may be comprised by multiple or an array of vectors.

The present invention represents a synergistic next generation approach to unmask specific phage-host interactions at all possible levels—ranging from nucleotide sequence to transcription to translation. The present invention thus provides a method for producing a phage/phage species/phage vector with bactericidal efficiency which can be applied to treating AMR-related diseases or infections. The present invention allows identification which phage genes are expressed, when, and how. Taking the whole picture of different gene expression at three infection stages, allows to predict the infection strategy patterns. Thus, gene markers can be designed to distinguish divergent phages with different infection strategies in the sorted VT (viral tagging)-phage-host pairs. This allows further gene-targeted phage isolation to provide phage nucleotides and proteins for downstream high-resolution analysis.

In one embodiment of the present invention, the bacterial cell with which the labelled phages is contacted in step (2) of the method of the present invention may be an antimicrobial resistance (AMR) bacterial cell. In this context, as used herein unless specified otherwise, "antimicrobial resistance" may be used interchangeably with "drug resistance" and comprises resistance to at least antibiotic agents known in the art, i.e. the ability of a bacterial cell to resist the effects of a drug or agent that could otherwise successfully treat said bacterial cell. Thus, the term "antimicrobial resistance" as used herein also comprises the term "antibiotic resistance" as known in the art.

The bacterial cell with which the labelled phages is contacted in step (2) of the method of the present invention may be any bacterial cell, eubacterial or archaebacterial, Gram$^+$ or Gram$^-$, and may be an AMR bacterial cell as described herein. In one embodiment of the present invention, the bacterial cell is pathogenic to mammals, particularly to humans. In a more specific embodiment of the present invention, the bacterial cell may be selected from the group consisting of *Helicobacter pylori, Haemophilus influencae,* and *Acinetobacter baumanii*. In a specific embodiment of the present invention, the bacterial cell is an *H. pylori* cell, preferably an AMR *H. pylori*.

In one embodiment of the present invention, the phage vector prepared in step (9) comprises no, or a reduced set of functional packaging genes compared to the natural phage comprising one or more of the candidate genes identified in step (8) and comprised by the phage vector prepared in step (9). Such packaging genes are generally known in the art. A non-limiting example of packaging genes in context with the present invention may comprise bacteriophage T4 gene 16 and/or 17 (cf. NCBI accession no. NC_000866.4).

In another embodiment of the present invention, one or more packaging genes are removed and/or mutated to result in a non-functional packaging gene, compared to the packaging genes of the natural phage comprising one or more of the candidate genes identified in step (8) and comprised by the phage vector prepared in step (9).

In a further embodiment of the present invention, the phage vector prepared in step (9) comprises beside at least one candidate gene identified in (8):

(a) one or more multiple receptor recognizing genes (to increase host range gene), e.g., by combining different receptor recognizing genes (e.g. gp17/37 of T-even type phages, gp38 of T-odd type phages, or Stf of A-like phages), (b) one or more genes interfering with quorum sensing mechanisms of the bacterial host cell (to inhibit hosts in low or high abundance), e.g., Agr B, Agr C or Agr D, (c) one or more genes encoding proteins which enable or improve disruption of biofilm formation, e.g., dspB gene, and/or (d) genes of anti-CRISPR system, e.g., genes encodes anti-CRISPR protein families AcrID1(Accession no. YP_009272954.1), AcrIE1(YP_007392738.1), AcrIE2 (YP_007392439.1), AcrIE3(YP_950454.1), AcrIE4 (NP_938238.1), AcrIF1(YP_007392342.1), AcrIF2 (NP_938237), AcrIF3(YP_007392440.1), AcrIF4

(WP_016068584.1), AcrIF5(YP_007392740.1), AcrIF6(WP_043884810), AcrIF7(ACD38920.1), AcrIF8(AFC22483.1), AcrIF9(WP_031500045.1), AcrIF10(KEK29119), AcrIIA1(WP_003722518.1), AcrIIA2(WP_003722517.1), AcrIIA3 (WP_014930691.1), AcrIIA4(WP_003723290.1), AcrIIA5(ASD50988.1), AcrIIC1(WP_049360089.1), AcrIIC2(WP_042743678.1), AcrIIC3 (WP_042743676.1), Aca1(YP_007392343.1), or Aca2 (WP_019933869.1), Aca3(WP_049360086.1).

The present invention further relates to a composition comprising a phage vector obtainable by the method as described and provided in context with the present invention. The present invention further relates to a composition comprising a phage vector obtained by the method as described and provided in context with the present invention.

The present invention further relates to a pharmaceutical composition comprising a phage vector obtainable or obtained by the method as described and provided in context with the present invention. Such pharmaceutical composition may further comprise pharmaceutically acceptable carriers as known in the art.

The present invention further relates to a pharmaceutical composition comprising a phage vector obtainable or obtained by the method as described and provided in context with the present invention for use in treating a disease caused by bacterial cells. Again, in context with the present invention, bacterial cells may be any bacterial cell, eubacterial or archaebacterial, Gram$^+$ or Gram$^-$. In one embodiment of the present invention, the bacterial cell is pathogenic to mammals, particularly to humans. In a more specific embodiment of the present invention, the bacterial cell may be selected from the group consisting of *Helicobacter pylori, Haemophilus influencae*, and *Acinetobacter baumanii*. In a specific embodiment of the present invention, the bacterial cell is an *H. pylori* cell. Also in this context, the bacterial cell may be an antimicrobial resistance (AMR) bacterial cell as described herein. In a specific embodiment of the present invention, the bacterial cell to be treated with the pharmaceutical composition described and provided herein, is an AMR *Helicobacter pylori, Haemophilus influencae*, or *Acinetobacter baumanii*, preferably an AMR *H. pylori*.

In a further embodiment, the pharmaceutical composition as described and provided in context with the present invention for use in treating a disease caused by bacterial cells further comprises at least one antibiotic and/or other pharmaceutical agents commonly used to treat a disease caused by said bacterial cells, e.g., for the case an (AMR) *H. pylori* being said bacterial cell, a proton pump inhibitor.

As used herein, unless specifically defined otherwise, the term "nucleic acid" or "nucleic acid molecule" is used synonymously with "oligonucleotide", "nucleic acid strand", or the like, and means a polymer comprising one, two, or more nucleotides, e.g., single- or double stranded.

Generally, as used herein, the terms "polynucleotide", "nucleic acid" or "nucleic acid molecule" are to be construed synonymously. Generally, nucleic acid molecules may comprise inter alia DNA molecules, RNA molecules, oligonucleotide thiophosphates, substituted ribo-oligonucleotides or PNA molecules. Furthermore, the term "nucleic acid molecule" may refer to DNA or RNA or hybrids thereof or any modification thereof that is known in the art (see, e.g., U.S. Pat. Nos. 5,525,711, 4,711,955, 5,792,608 or EP 302175 for examples of modifications). The polynucleotide sequence may be single- or double-stranded, linear or circular, natural or synthetic, and without any size limitation. For instance, the polynucleotide sequence may be genomic DNA, cDNA, mitochondrial DNA, mRNA, antisense RNA, ribozymal RNA or a DNA encoding such RNAs or chimeroplasts (Gamper, Nucleic Acids Research, 2000, 28, 4332-4339). Said polynucleotide sequence may be in the form of a vector, plasmid or of viral DNA or RNA. Also described herein are nucleic acid molecules which are complementary to the nucleic acid molecules described above and nucleic acid molecules which are able to hybridize to nucleic acid molecules described herein. A nucleic acid molecule described herein may also be a fragment of the nucleic acid molecules in context of the present invention. Particularly, such a fragment is a functional fragment. Examples for such functional fragments are nucleic acid molecules which can serve as primers.

The level of identity between two or more sequences (e.g., nucleic acid sequences or amino acid sequences) can be easily determined by methods known in the art, e.g., by BLAST analysis. Generally, in context with the present invention, if two sequences (e.g., polynucleotide sequences or amino acid sequences) to be compared by, e.g., sequence comparisons differ in identity, then the term "identity" may refer to the shorter sequence and that part of the longer sequence that matches said shorter sequence. Therefore, when the sequences which are compared do not have the same length, the degree of identity may preferably either refer to the percentage of nucleotide residues in the shorter sequence which are identical to nucleotide residues in the longer sequence or to the percentage of nucleotides in the longer sequence which are identical to nucleotide sequence in the shorter sequence. In this context, the skilled person is readily in the position to determine that part of a longer sequence that matches the shorter sequence. Furthermore, as used herein, identity levels of nucleic acid sequences or amino acid sequences may refer to the entire length of the respective sequence and is preferably assessed pair-wise, wherein each gap is to be counted as one mismatch. These definitions for sequence comparisons (e.g., establishment of "identity" values) are to be applied for all sequences described and disclosed herein.

Moreover, the term "identity" as used herein means that there is a functional and/or structural equivalence between the corresponding sequences. Nucleic acid/amino acid sequences having the given identity levels to the herein-described particular nucleic acid/amino acid sequences may represent derivatives/variants of these sequences which, preferably, have the same biological function. They may be either naturally occurring variations, for instance sequences from other varieties, species, etc., or mutations, and said mutations may have formed naturally or may have been produced by deliberate mutagenesis. Furthermore, the variations may be synthetically produced sequences. The variants may be naturally occurring variants or synthetically produced variants or variants produced by recombinant DNA techniques.

"Deviations" from sequences (e.g., amino acid or nucleic acid sequences) as used herein may comprise, e.g., deletions, substitutions, additions, insertion and/or recombination. The term "addition" refers to adding a nucleic acid residue/amino acid to the end or beginning of the given sequence, whereas "insertion" refers to inserting a nucleic acid residue/amino acid within a given sequence. The term "deletion" refers to deleting or removal of a nucleic acid residue or amino acid residue in a given sequence. The term "substitution" refers to the replacement of a nucleic acid residue/amino acid residue in a given sequence. Again, these definitions as used here apply, mutatis mutandis, for all sequences provided and described herein unless specified otherwise.

In accordance with the present invention, as used herein in context with amino acid sequences, the term "similar" means that a given amino acid sequence comprises identical amino acids or only conservative or highly conservative substitutions compared to the amino acid sequence of the respective sequence to be compared. As used herein, "conservative" substitutions mean substitutions as listed as "Exemplary Substitutions" in Table I herein. "Highly conservative" substitutions as used herein mean substitutions as shown under the heading "Preferred Substitutions" in Table I herein.

TABLE I

| Amino Acid Substitutions | | |
| --- | --- | --- |
| Original | Exemplary Substitutions | Preferred Substitutions |
| Ala (A) | val; leu; ile | Val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; | leu |
| Leu (L) | norleucine; ile; val; met; ala; | ile |
| Lys (K) | arg; gin; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | Phe |
| Val (V) | ile; leu; met; phe; ala; | leu |

As used herein, "silent" mutations mean base substitutions within a nucleic acid sequence which do not change the amino acid sequence encoded by the nucleic acid sequence. "Conservative" substitutions mean substitutions as listed as "Exemplary Substitutions" in Table I. "Highly conservative" substitutions as used herein mean substitutions as shown under the heading "Preferred Substitutions" in Table I.

The embodiments which characterize the present invention are described herein, shown in the Figures, illustrated in the Examples, and reflected in the claims.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% or 2% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

FIGURES

Figure 2:
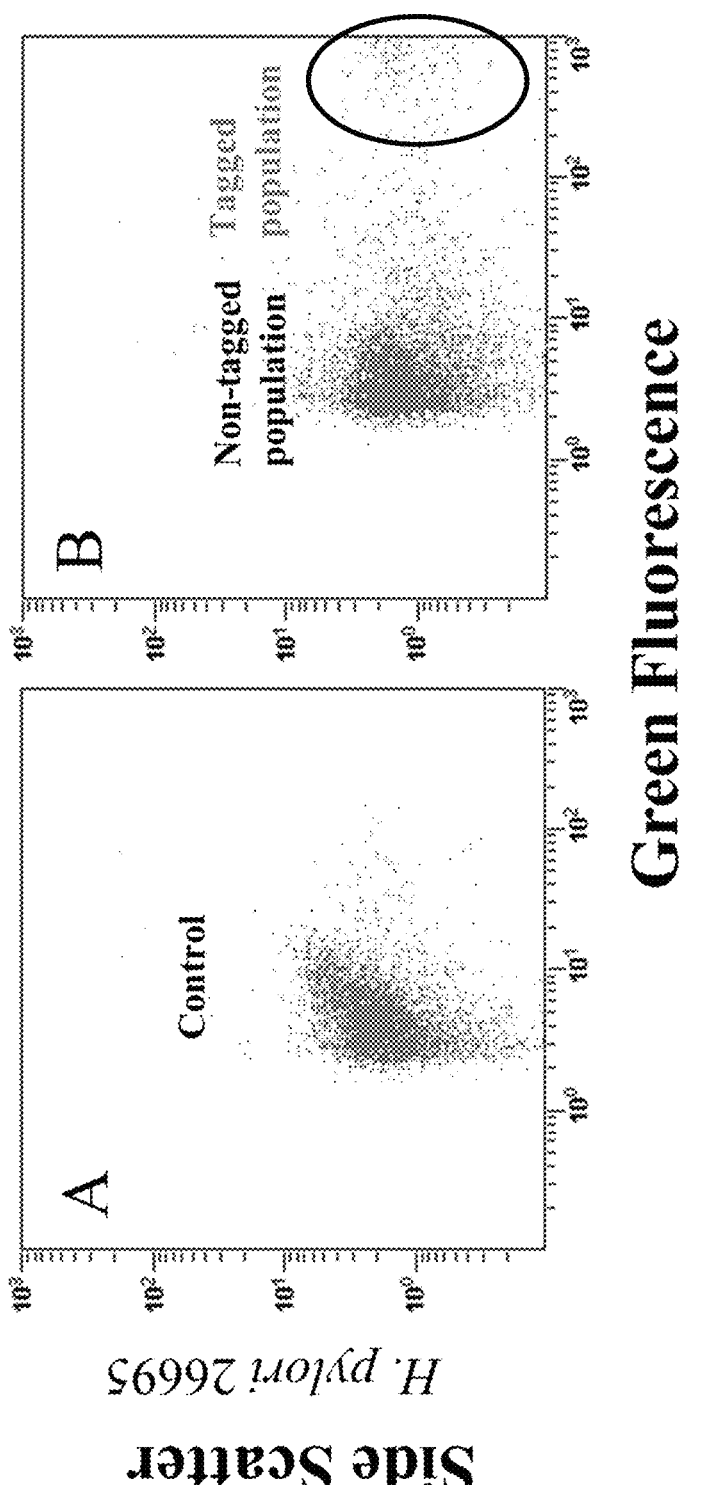

The Figures show:

FIG. 1 Systematic experimental setup to identify the phage-host interaction at the level of genes, transcription & translation FIG. 2 Flow cytometry data triggered on Side scatter (SSC) for the fluorescently labelled phages. A. Controls of *H. pylori* 26695; B. fluorescently labelled virus co-incubated with cells at a virus-to-bacteria-ratio (VBR) of 1. Code: circled=viral-tagged bacteria population; non-circled=non-tagged bacteria.

The present invention is further illustrated by the following examples. Yet, the examples and specific embodiments described therein must not be construed as limiting the invention to such specific embodiments.

EXAMPLES

Sample Collection and Control Cultures

Environmental Samples Collection

Environmental samples were collected from four different aquatic habitats: the income water tank of a wastewater treatment plant (Gut Großlappen, Munich, Germany), an on-site groundwater collection well (48° 13'25.8"N 11° 35'45.4"E, Munich, Germany), a lake (Feldmochinger See; 48° 12'56.0"N 11° 30'49.4"E, Munich, Germany), and a river (Isar; 48° 32'59.3"N, 12° 10'42.4"E, Landshut, Germany). Samples were transported in the dark on ice within 2 hours. To remove particles the size of bacteria and larger, all water samples were filtered with 0.22 μm syringe filters (Millex-GP) and were frozen at –80° C. immediately after filtration.

Clinical Sample Collection

Eleven healthy human volunteers provided faecal samples (5-30 g) in sterile collection containers, which were frozen at –80° C. immediately after collection or stored up to 18 hours at 4° C. before freezing.

Bacteriophage Cultures

Five *Escherichia coli* and *Pseudomonas aeruginosa* specific phages were used as assay controls in the present study: MS2 (DSM 13767), T4 (DSM 4505), T7 (DSM 4623), M13 (DSM13976), Lambda phage (DSM4499) and φX174 (DSM 4497). The genomic and structural properties of the phages as well as their bacterial hosts have been well characterized previously. For preparation of the virus isolate stocks, the respective bacterial host was grown in sterile LB medium (LB broth Miller, Sigma-Aldrich, St. Louis, Mo.) until an optical density of 0.3 measured at 600 nm was reached, then inoculated with phages at a virus-to-bacteria-ratio of 0.1, followed by overnight incubation. Virus stocks were filtered with 0.22 μm syringe filters (Millex-GP, Merck-Millipore, Billerica, Mass.) and filtration was repeated prior preparation of samples for measurements.

VT Experimental Details

Viral Stain and Wash

Dyes used to stain viruses, e.g. SYTO 9, SYBR Gold, SYBR Green II and SYBR Safe, were diluted to 50× in TE buffer (10 mM Tris, 1 mM EDTA; pH 8.0) for storage in –20° C. in the dark until dilution to final concentration of 1-5× for preparation of viral particles for VT. Cf. Džunková et al. (Nature Microbiology (2019), DOI: 10.1038/s41564-019-0526-2) for labeling clinical samples. Viral samples were stained with dyes at 30° C. for 30 min for the environmental samples. The ultracentrifugal devices (100 KDa cut-off; Amicon) were pretreated by incubating 1.5 ml of 0.2 μm-filter-sterilized 1% BSA (Bioexpress, UT, cat #E531-1.5 ML) in phosphate buffered saline (PBS) for 1 h at room temperature. Stained water samples were washed six times by phage buffer in the pretreated ultracentrifugal devices. 50 μl phage buffer were added back for every 500 ml viral samples and sonicated (VWR Signature Ultrasonic cleaner B1500A-DTH, VWR) for 3 minutes using the settings of 50 W at 42 kHz, resulted a 10-fold concentration of viruses from the original sample. Stained and washed viruses were mixed with bacteria at concentrations and ratios desired for flow cytometer analysis, typically $10^5$ cells per ml. VT experiments were done with a negative control, which was prepared identically to the stained and washed virus samples except without viruses; this controlled for free dye creating the appearance of false positive 'viral tagged cells'. Filamentous phage M13 propagated on *E. coli* was used as a standard cross control for flow cytometry and the VT assays, as well as the lytic DNA phages T4, T7, Lambda and φX174 with their respective *E. coli* host strains as positive control for tagging and the sorter working conditions.

The concentration of bacterial cells or viral particles to be combined in the VT assay was then adjusted by saline solution (SS, 0.9% NaCl) to obtain a ratio of ~100:1 to 1:100 (bacteria to phage), where >1.000 cells/sec were processed by FACS. Six 200 μl aliquots of the washed and diluted cell preparation were used as: 1) unstained bacterial cells mixed with SS, 2) stained bacterial cells mixed with SS, 3) unstained bacterial cells mixed with unstained M13 phage, 4) unstained bacterial cells mixed with stained M13 phage, 5) unstained bacterial cells mixed with unstained sample viruses, and 6) unstained bacterial cells mixed with stained sample viruses (VT samples). Bacterial cells for mixture 2 were stained with one microliter of dye, diluted 10× in sterile water, and incubated at room temperature in the dark for 30 min. Mixtures 1 to 5 were used as sorting controls and mixture 6 was the VT sample. All mixtures were incubated at 30° C. for 1 hour with mild rotary shaking to prevent sedimentation, and sample volumes were subsequently adjusted to 1 ml with SS before sorting using FACS. Non-specifically bound viruses were removed.

Flow Cytometry Analyses and Sorting

Samples were examined using an iCyt Reflection flow cytometer equipped with a 200 mW 488 nm air-cooled solid-state laser or a MoFlo™ XDP (Beckman Coulter) cytometer. Fluorescence was detected using a 520/40 band pass filter with an amplified photomultiplier tube. Events were detected using a Forward Scatter trigger, and data collected in logarithmic mode then analyzed with WinList 6.0 software (Verity software house). Fluorescent polystyrene FLOW Check™ microspheres (1 μm yellow-green beads; Polysciences Inc., PA, cat #23517-10) were used as an internal standard. Samples were typically run with a concentration of $10^5$ cells ml$^{-1}$.

The negative sorting controls were processed first in the following order: unstained bacterial cells, bacterial cells mixed with unstained M13 phage, bacterial cells mixed with unstained viruses, and bacterial cells mixed with stained M13 phage. The VT samples containing bacterial cells mixed with stained viruses were then processed, with 10,000 events usually recorded per sample to identify sorting gates which did not overlap with the negative controls. The final sample processed prior to sorting was the stained bacterial cell control to confirm that there was no overlap with the identified VT sorting gates. The flow cytometer was then cleaned prior to sorting of VT samples by repeatedly backflushing the fluidics and processing an ultra-pure water sample. For multi-cell sorts (50,000 or 100,000 cells), cells were collected in 1.5 ml low-bind tubes. For single-cell sorts, cells were sorted into 96 or 384 well plates with single-cell mode settings. The first, third and last column of the plate were left empty as negative controls, while 100 cells were collected into the second column as a positive amplification control. All sorted cells were stored at –80° C. until further processing. Flow cytometry (.fsc) files were processed for visualisation using FlowViz and FlowCore R packages.

VT Metagenomic Sequencing

Either VT or purified community viral samples were combined with 10 μl of DNAse I buffer and 5 μl of DNAse I (Sigma-Aldrich, #AMPD1-1KT) and incubated for 15 min at room temperature to degrade free bacterial DNA in the viral filtrate. DNAse was inactivated by adding 10 μl DNAse stop solution and incubation at 70° C. for 10 min. Viral DNA was then extracted using a low biomass DNA extraction method, which could also be applied to single cells (see below) (see, e.g., Džunková et al., loc cit. for viral DNA extraction). All reagents used in the DNA extraction were autoclaved, sterilized by 0.1 μm filtration and UV-radiated for 60 min. Each DNAsed virion sample (110 μl) was mixed with 77 μl of Lysis buffer prepared by combining 700 μl KOH stock (0.43 g/10 ml), 430 μl DDT stock (Thermo Fisher, #R0861, 0.8 g/10 ml) and 370 μl water, final pH 12. The sample was incubated for 10 min at room temperature, −80° C. for one hour and 55° C. for 5 min to complete virion lysis. The alkaline reaction was then neutralized by adding 77 μl of Stop buffer (5 g Tris-HCl in 10 ml, pH 4.5) and 1 μl of Proteinase K (20 mg/ml, Sigma-Aldrich, #3115887001) was added to the sample and incubated for 30 min at 55° C. The DNA was purified using 536 μl (1.8× sample volume) Agencourt AMPure beads (Beckman Coulter, #A63880) according to the manufacturer's instructions. Each sample was finally resuspended in 30 μl of sterile water.

Purified viral DNAs were checked for contaminating prokaryotic or eukaryotic DNA by PCR amplification of 16S rRNA genes, 18S rRNA genes and human mitochondria Positive controls used were E. coli and human gDNA diluted to 0.01 ng/μl and virion-free DNA extractions used as negative controls.

An optimised protocol for ultra-low input samples (cf. Rinke et al., Peer J (2016), 4: e2486) was used to prepare libraries for sequencing on the NextSeq platform. Approximately 2 GB of 2×150 bp sequence data was obtained per sample.

4sU-Labeling, 4sU-Seq and RNA-Seq

Metabolic labelling of newly transcribed RNA with 4sU (Carbosynth, NT0618690) at the early, middle and late infection stage, RNA isolation and biotinylation was performed as described before (Rädle et al., loc. cit.) with minor changes. 500 μM 4sU was used for 0.5 h of labelling and 200 μM 4sU was used for 1 h labelling. The newly transcribed RNA was eluted into 400 μl Agencourt RNAClean XP Beads (Beckman Coulter) and continued with the recovery following the manufacturer's instructions. RNA was eluted in 11 μl nuclease-free $H_2O$ and quantified using Qubit 2.0 Fluorometer.

For both, total and 4sU RNA samples, library preparation and rRNA depletion was performed using the TruSeq Stranded Total RNA Library Prep Kit (Illumina) starting with 400 ng RNA as input for each sample. Only 11 cycles were used for PCR amplification to minimize PCR bias. Amplified cDNA libraries were further purified using Agencourt RNAClean XP Beads (Beckman Coulter) and quality control of biotinylated RNA and cDNA libraries were performed using Agilent Bioanalyzer with RNA 6000Nano Reagents (Agilent Technologies, 5067-1511) or High Sensitivity DNA Reagents (Agilent Technologies, 5067-4626). Barcoded libraries were sequenced on a HiSeq 2500 (Illumina) with paired-end, 100 bp reads.

Bioinformatics Analysis

Quality Control (QC)

Illumina data quality-control consisted of trimming ends with a quality score lower than 25 as well as sequences containing ambiguous bases, only reads longer than 100 bp were kept. Additionally, because the Illumina sequencing was done from linker-amplified DNA, it was mixed 1:1 with phiX174 DNA to minimize base-calling issues in Illumina software. Thus full-length reads matching (>98% identity) to the phiX174 genome were removed and the remaining reads were considered our target material, linkers removed and quality controlled (cf. Deng et al., Nature (2014), 513: 242-245).

Assembly

Contigs were assembled from post-QC reads using Velvet (Version 1.2.01) with a conservative k-mer size of 57 and the −cov cutoff option set to 10 as done previously (Hess et al., Science (2011), 331: 463-467). Iterative assembly was used whereby reads incorporated into the largest contigs were removed in to compensate for highly variable coverage (30-500×) found across the genomes in these natural samples. After 15 rounds of assembly, 26 large contigs were obtained (>30 kb that were 'representative' regions of the genome, see below) and referred as Candidatus Genomes' (GCs) in the manuscript. These 26 CGs utilized a total of ~40% of the available reads; the remaining 60% of the data presumably belong to rare members of this coastal phage community.

Protein Clustering

Open reading frames (ORFs) were predicted using prodigal (cf. Richards et al., Infect Genet Evol (2011), 11: 1263-1275) from all contigs >1.5 Kb, including the CGs, as well as on all 454 reads that were not used in assembly. ORFs were clustered using CD-HIT (cf. Devirgilliis et al., Genes Nutr (2011), 6: 275-284) with a cutoff of 75% identity. Individual reads then were mapped to protein clusters using BLASTn, and evalue cutoff of 0.001, only non-redundant top hits were used. Rarefaction curves were calculated using a custom perl script (Rarefaction.pl). Chao-1 index was calculated from the protein cluster data as described in Chao and Lee (J A Stat Assoc (1992), 87: 210-217). Simpson diversity index (D) (see Simpson, Nature (1949), 163: 688) was calculated as $D=\Sigma n(n-1)/N(N-1)$. Shannon-Wiener ($H'=-\Sigma p$ In p), was calculated using PHACCS (see above) (cf. Angly et al., BMC Bioinformatics (2005), 6: 41).

Contig Annotation

Assembled contigs >1.5 Kb were annotated as follows: ORFs were predicted using Prodigal (above) and functionally annotated using manually curated data resulting from BLASTp analyses against the non-redundant protein database of Genbank, and custom databases of T4 phage gene clusters (T4-GCs) (cf. Sullivan, Environ Microbiol (2010), 12: 3035-3056) and Microbial Metabolic Genes (cf. Sharon et al., ISME J (2011), 5: 1178-1190). To estimate the relative proportion of reads associated with particular viral types, a BLASTx search was used against the phage genomes available in NCBI, and assigned taxonomy to metagenomic reads by the taxon lineage associated with their top hit (requiring e-value <1 e-3), read2family.pl available was used with the rest of the scripts.

Whole Genome Comparisons and Statistical Assessment

To estimate the relatedness of the new whole genomes and CGs generated in this study, commonly used metrics for microbial genome comparisons were adopted—average nucleotide/amino acid identity (ANI/AAI; cf. Konstantinidis et al., loc cit.). For the broader comparisons, AAI rather than ANI was used due to the low nucleotide conservation across viral genomes. First, in silico 'sizing' and 'positioning' evaluations were performed to empirically determine how to interpret fragmented genomes resulting from VT metagenomic assemblies using a custom perl script (SizeAndLocation.pl). Specifically, fragments (20, 25, 30, 35, 40, 45, 50 and 55 Kb) were generated from each complete genome on a sliding window of 5 kb. The ANI between the fragment and a database of full genomes was then calculated. A custom script (Pearsons.pl) was used to compare the resulting vector (similarity profile) of ANI values (fragment vs genomes) to that of the full genome (genome vs genomes). The result was converted to a correlation-based distance ($=1-r$, where r corresponds to Pearson's correlation coefficient; only positive values of r where obtained) to assess how well any given fragment represents a full genome. Then the genetic relatedness of all CGs from the VT metagenome was compared using AAI, against a fixed database of reference phage genomes. Also, to estimate the variability within a population from the available metagenomic data, random CGs were generated as follows using a custom perl script. First, reads requiring at least 95% identity and a coverage of 95% of the length of the read (Recruit2CloudV1.pl) were recruited. Each read was non-redundantly assigned and aligned to genomes using default parameters with MUSCLE (cf. Edgar, BMC Bioinformatics (2004), 5: 113). For each population, 100 random genome fragments were generated using the metagenomic data that went into generate the consensus sequence where each base has a probability of being assigned at any given position based on its occurrence. AAI was calculated only from conventionally defined pairs of homologous genes. Homology was defined when the sequence similarity was over 40% and covered at least 60% of the length of the shortest genome. The matrix of pairwise AAI genome comparisons was used in principal component analysis. The Euclidian distances of the reference genomes in this three-dimensional coordinate system are a good proxy for their phylogenetic relationships.

The clusterness of the VT data was assessed using the following approaches: First, the accuracy of the assignment, Q was defined. The distances between each random sequence and each of the consensus sequences was calculated, each randomly generated sequence was assigned to the consensus that was closest to it. Only the first three coordinates were used as 3 PCs account for 75% of the variation and serve as a good proxy for phylogenetic distances. This information was compiled in an assignment matrix A, where rows are the actual consensus sequence sources and the columns are the assigned (closest) sequences. If the random sequences are highly similar to the source, then the assignment matrix should be nearly diagonal. The accuracy of the assignation is defined as $Q=Tr(A)/N$, where N total number of randomizations and $Tr(A)$ denotes the trace of the matrix A. Alternatively, Q is equivalent to the fraction of true positive assignations (i.e., the number of times in which a genome was correctly assigned to its true source divided by the total number of generated genomes). To statistically evaluate the significance of the observed value of Q we used a randomization scheme as follows (Acc.m and AccRdm.m): Labels were randomly assigned to fragments, then Q was calculated as above, this was done 1000 000 times, in no case we obtained a higher value of Q than the observed. Then the effect size was measured in terms of a Z-score, $Z=(Q_e-Q_r)/\sigma$, where $Qe=0.9906$ is the observed Q value, $Qr=0.0665$ is the average value of the randomization scheme and a is the standard deviation of Q values in the randomization scheme, $\sigma=0.0065$, $Z=142.17$. This Z score implies that the observed Q is very far from any observed value obtained by random chance.

Since a value of Q close to 1 can result from loose clusters that are well separated in space, the compactness of the cluster was also calculated. To do this, the Dunn index (dunns.m and DunnRdm.m) (cf. Dunn et al., Cybernet Syst (1973), 3: 32-5721] was used. Briefly, this index corresponds to the ratio of the smallest distance between all pairs of clusters divided by the maximum distance within a cluster. A similar randomization scheme as stated above was run; out of 1,000,000 repetitions, the measured Dunn index of the CGs data was larger than that observed in any of the randomization trials. The Z-score for the Dunn index was 1829, again suggesting the observed Q is highly unlikely to be random.

Locus-by-Locus Variation

To get beyond genome-wide averaged genetic diversity metrics, the underlying sequence data for each population was examined to estimate variation at the level of a predicted ORF. Those reads mapped to reference genomes (95% identity over 95% read length) were further examined to determine the locus-by-locus genetic diversity (average pairwise percent nucleotide identity per ORF) using a custom perl script (LocusbyLocus.pl). While most loci in these populations are nearly 100% identical, box plots (0.09, 0.91, second and third quartile and median) showed the range of variability in the identity of reads assigned to each locus.

RNA Analysis

For 4sU and total RNA, reads were mapped against assembled CGs using ContextMap version 2.5.2 (Bonfert et al., loc cit) [ ] in paired-end mode. To calculate FPKM (Fragments Per Kilobase Of Exon Per Million Fragments Mapped) values, fragment counts per gene were calculated using the featureCounts program from the subread package version 1.4.6-p3 (Liao et al., Bioinformatics (2014), 30(7): 923-930).

FPKM values were additionally normalized by the median fold changes of housekeeping genes. Only genes with an FPKM>1 in at least one sample for 4sU-Seq and total RNA-Seq were included in the analysis. For visualization, mapped reads were converted to bedGraph using the HOMER software suite version 4.8.3 (Heinz et al., 2010) and visualized in the UCSC genome browser (Kent et al., 2002). Peaks were called over input using MACS2 version 2.1.0 (Zhang et al., 2008) with an FDR threshold of 0.05. RNA Pol II promoter and gene body FPKM was determined as for RNA-Seq by counting reads with featureCounts on the promoter (TSS±500 nt) or the gene body (including exons and introns) and normalizing to promoter/gene length and sequencing depth.

Primer Design for Targeted Phage Isolation

Candidate marker genes of each CG cluster were selected by following means: Selection of (i) conserve ORF shows the highest ANI within one cluster, as well as <75% ANI to those of other clusters, and/or (ii) ORFs exhibiting at least 2-fold expression in early and late infection stages compared to the average expression level of all RNAs. Primers were designed to amplify 100-400 bp amplicons in locations where an Adenine (A) base exist at the 3' position of the final primer sequence (after barcode assembly). Primer3 with default settings were used for primer design targeting marker genes, but modified its internal primer predictions such that it enforces primer's 3' to end with a T nucleotide. Amplicon sizes of minimum 75 nt and maximum 248 nt were aimed for compatibility with 2×150 bp paired end sequencing. Rounds of primer validation and replacement were conducted to reach to an optimal set.

Targeted Phage Isolation

Repeat of the VT single-cell sorts, and cells were sorted into 96 well plates (Plate A) pre-filled with 10 μL host bacteria suspension in SS, using single-cell mode settings. The first, third and last column of the plate were left empty as negative controls. Plates were incubated in 37° C. overnight allowing cell proliferation and then stored in 4° C. up to two days. Five μL from each well were transferred to a $2^{nd}$ 96 well plate (plate B) pre-filled with two μL reverse transcription mixture (RT mix) which was prepared using SuperScript™ III First-Strand Synthesis System (Invitrogen) including reverse transcriptase at a final concentration of 2.5 U/μL and primers in nuclease-free water. The reverse transcription was performed using the thermocycler program: 50° C. for 50 min, and 85° C. for 5 min, skipping RNaseH addition step.

Barcoding

Klenow Fill-in Reaction: Klenow fill-in reaction mixtures were prepared in nuclease-free water by combining 1× React® 2 Buffer (Invitrogen), 0.267 mM dNTPs, 2.5 μM multiplexed rc-primer mix, 2.5 μM barcode and 0.0167 U/μL DNA Polymerase I large (Klenow) fragment (Invitrogen). The reaction was incubated at 25° C. for 1 h. A variation of this reaction included 3.75 μM multiplexed rc-primer mix, 3.75 μM barcodes, and 0.033 U/μL Klenow fragment, with incubation at 25° C. for 2 h. Klenow was inactivated by incubation at 80° C. for 10 min. Reverse complementary strand was removal by lambda exonuclease (1× Reaction Buffer and 0.33 U/μL Lambda Exonuclease (NewEngland Biolabs)), and incubated at 37° C. for 30 min, then at 80° C. for 10 min.

Pre-Amplification PCR: Unit PCR reaction (10 μL total) consisted of 2.5 μL (0.5× final) Platinum® Multiplex PCR Master Mix (Applied Biosystems), 1.8 μL 25 mM MgCl2 (4.5 mM final), 1.5 μl Forward lambda reaction product (non-purified), 1.5 μl Reverse lambda reaction product (non-purified), 2 μL cDNA, and 0.7 μL nuclease-free water (not DEPC-treated). The reaction cycle was as follows: initial denaturation at 95° C. for 5 min; 22 cycles of 95° C. for 30 sec, 60° C. for 3 min, 72° C. for 60 sec; and final extension at 68° C. for 10 min. Unit PCR reactions of genotyping assays were 20 μL, with the same concentration of reagents, and 18 cycles of PCR.

qRT-PCR and Melting Curve Analysis qRT-PCR analyses were performed using nested primers targeting the amplicons, excluding the barcodes and the adapters. Unit reaction (10 μL total) consisted of 5 μL (1× final) Power SYBR™ Green PCR Master Mix (Applied Biosystems), 1 μL pre-amplification PCR product, 1 μL forward and reverse nested primers mix (each 0.2 μM final), and 3 μl nuclease-free water (not DEPC-treated). The qRT- PCR cycle was as follows: initial denaturation at 95° C. for 10 min; followed by 35 cycles of 95° C. for 15 sec and 60° C. for 1 min. Melting curve analysis was done by heating the amplicons from 60° C. to 95° C., incrementing 0.05° C./s. All the reactions were run as three replicates. PCR products were pooled in nuclease-free falcon tubes (Ambion), mixed with 0.1 volume 3 M NaOAc (pH 5.5) (Ambion) and 2.5 volume 100% ethanol (molecular biology grade), and kept at −20° C. overnight for precipitation. Balk RNA were extracted and barcoded libraries were sequenced on a HiSeq 2500 (Illumina) with paired-end, 100 bp reads as previous RNA section.

Phages in respective wells of Plate A of those in Plate B with positive yields were selected for phage cultivation and cultivated at 37° C. for 24 hrs (Plate C).

Expression in *P. aeruginosa*

All phage genes were cloned in a Gateway entry vector using the pENTR/SD/D-TOPO cloning kit (Invitrogen). Subsequently, the genes were transferred to the *E. coli-P. aeruginosa* shuttle expression vector pUC18-mini-Tn7T-Lac (Choi et al., Nat Methods (2005), 2: 443-448), which was made Gateway compatible. Co-transformation of 250 ng of the pUC18-mini-Tn7T-Lac constructs and pTNS2 by electroporation to *P. aeruginosa* PAO1 or PA14 (Choi et al., J Microbiol Methods (2006), 64: 391-397) allowed single-copy integration of the phage proteins in the *Pseudomonas* genome under the control of an IPTG-inducible lac promoter which was verified using PCR and DNA sequencing (Choi et al., 2005).

*E. coli* and *P. aeruginosa* cells were grown at 37° C. in Lysogeny Broth (LB) and on LB, artificial sputum medium (Sriramulu et al., J Med Microbiol (2005), 54: 667-676) or M9 minimal medium (Sambrook and Russell, 2001, Molecular Cloning, Cold Spring Harbor, N.Y.: Cold Spring Harbor Laboratory) plates, supplemented with 0.1 mg ml⁻¹ ampicillin, 0.03 mg ml⁻¹ gentamicin and/or 1 mM IPTG, if required. As negative and positive control in the expression experiments, *P. aeruginosa* cells containing an empty vector construct and inhibitory protein, respectively, were used. Growth curves were generated using a Nanodrop one spectrophotometer (ThermoFisher).

Phage Vector Synthesis

Cell Free System and T4 TXTL Reactions

New phages were engineered using *E. coli* TXTL system (myTXTL, Arbor Biosciences) as previously described (Shin et al., loc. cit.). Transcription and translation were performed by the endogenous molecular components provided by an *E. coli* cytoplasmic extract, without addition of exogenous purified TXTL molecular components. TXTL reactions were composed of an energy buffer and 20 canonical amino acids solution. The energy buffer was composed of 50 mM Hepes pH 8, 1.5 mM ATP and GTP, 0.9 mM CTP and UTP, 0.2 mg/ml tRNA, 0.26 mM coenzyme A, 0.33 mM NAD, 0.75 mM cAMP, 0.068 mM folinic acid, 1 mM spermidine, 30 mM 3-PGA, either 10-15 mM maltose or 20-40 mM maltodextrin. A typical cell-free reaction was composed of 33% (v/v) of *E. coli* crude extract. The other 66% of the reaction volume was composed of the energy mixture, the amino acids and plasmids. The controls included two assays based on rifampicin (122 μM), an inhibitor of the core RNA polymerase, and DNase I (1 μg/ml).

Plaque Assay (PA)

The PA was used to confirm the infectivity of the newly engineered phages using a soft agar overlay technique as described elsewhere (Adams, Interscience Publishers (1959), NY). Briefly, 0.5 mL of appropriate dilutions of phages were mixed with an equal volume of fresh cultures of the corresponding hosts, grown overnight (incubated in LB medium at 37° C. until an optical density of 0.3 measured at 600 nm was reached). The phage-bacteria-suspension was mixed with 3 mL warm soft agar (0.75% w/v agar and 2.5% w/v LB) and gently poured on a petri dish already containing an LB agar layer (1.5% w/v agar and 2.5% w/v LB) in biological and technical replicates. Upon solidification, the petri dishes were inverted and incubated overnight at 37° C. After 15-20 h, depending on the bacterial growth efficiency, the plaques formed were manually counted and the phage titers as plaque-forming units per mL (PFU mL$^{-1}$) were calculated.

The invention claimed is:

1. A method for preparing a bactericidal phage vector, comprising the following steps:
   (1) Labelling phages,
   (2) Contacting the labelled phages of (1) with bacterial cells, for which a bactericidal effect of said bactericidal phage vector is desired, under conditions which allow infection of said bacterial cells with said labelled phages,
   (3) Identifying and separating infected bacterial cells with labelled phages,
   (4) Metagenomic sequencing of the phages in infected bacterial cells of (3), including bioinformatics analysis to map the genetic relatedness of phages of (3) according to i) their nucleic acid similarity or identity levels; or ii) their amino acid sequence similarity or identity levels; or iii) a combination of i) and ii), and allocate phages of (3) into genetic clusters based on i) said nucleic acid similarity or identity levels; or ii) said amino acid sequence similarity or identity levels; or iii) a combination of i) and ii), wherein the phages in one of the genetic clusters show a sequence identity of >75% with other phages in the genetic cluster,
   (5) 4-thiouridine (4-sU)-and total metatranscriptomic sequencing of RNA of early, middle and late expressed phage genes in the phages in infected bacterial cells of (3), and mapping RNA reads to the sequences of (4),
   (6) Selecting two or more suitable marker genes allowing phage isolation from infected bacterial cells with labelled phages of (3), wherein:
      (a) the suitable marker genes are open reading frames (ORFs) showing >bout 95% average nucleotide identity (ANI) or average amino acid identity (AAI) within one genetic cluster of (4) and <about 75% ANI or AAI compared to one or more other genetic clusters of (4); and (b) the suitable marker genes are ORFs exhibiting at least 3-fold higher expression in early and late infection stages compared to the average expression level of all RNAs from the early, middle, and late expressed phage genes of (5), optionally followed by further bioinformatic analysis for potential further functions of the marker gene,
   (7) Targeted phage isolation based on said two or more selected suitable marker genes of (6),
   (8) Identification of candidate marker genes, being considered said selected suitable marker genes of (6), which exhibit bactericidal activity on the infected host cell by applying i) gene-by-gene or protein-by-protein laboratory evaluation on bactericidal effect; ii) bioinformatics predictions of the function of each candidate marker gene based on annotations; or iii) a combination of i) and ii), and
   (9) Preparing a phage vector comprising one or more candidate marker genes of (8).

2. The method of claim 1, wherein said phages labelling in step (1) is selected from the group consisting of fluorescent labelling, antibody labelling and radioactive labelling.

3. The method of claim 1, wherein said bacterial cell is an antimicrobial resistance (AMR) bacterial cell.

4. The method of claim 1, wherein said bacterial cell is selected from the group consisting of *Helicobacter pylori*, *Haemophilus influenzae*, and *Acinetobacter baumanii*.

5. The method of claim 1, wherein in step (6) at least two different marker genes are selected which exhibit >about 95% ANI within one cluster of (4), and not more than 65% ANI compared to one or more other clusters of (4).

6. The method of claim 1, wherein the phage vector prepared in step (9) comprises no, or a reduced set of one or more functional packaging genes compared to the natural phage comprising one or more of the candidate marker genes identified in step (8) and comprised by the phage vector prepared in step (9).

7. The method of claim 6, wherein one or more packaging genes are removed and/or mutated to result in a non-functional packaging gene compared to the packaging genes of the natural phage comprising one or more of the candidate marker genes identified in step (8) and comprised by the phage vector prepared in step (9).

8. The method of claim 1, wherein the phage vector prepared in step (9) comprises additionally:
   (a) one or more multiple receptor recognizing genes,
   (b) one or more genes interfering with quorum sensing mechanisms of the bacterial host cell,
   (c) one or more genes encoding proteins which enable or improve disruption of biofilm formation, and/or
   (d) genes of anti-CRISPR system.

9. A composition comprising the bactericidal phage vector obtained by the method of claim 1.

10. A pharmaceutical composition comprising the bactericidal phage vector obtained by the method of claim 1.

*   *   *   *   *